(12) United States Patent
Espinosa Baruque et al.

(10) Patent No.: US 11,040,277 B2
(45) Date of Patent: Jun. 22, 2021

(54) DISPLAY OF A THREE DIMENSIONAL RECORDING IN A SYSTEM FOR REHABILITATION

(71) Applicants: Pablo Espinosa Baruque, Tres Cantos (ES); Maria Del Rosario Ortin Ramon, Tres Cantos (ES)

(72) Inventors: Pablo Espinosa Baruque, Tres Cantos (ES); Maria Del Rosario Ortin Ramon, Tres Cantos (ES)

(73) Assignee: FOREN METHOD S.L., Madrid (ES)

( * ) Notice: Subject to any disclaimer, the term of this patent is extended or adjusted under 35 U.S.C. 154(b) by 0 days.

(21) Appl. No.: 16/488,229

(22) PCT Filed: Feb. 23, 2018

(86) PCT No.: PCT/EP2018/054480
§ 371 (c)(1),
(2) Date: Aug. 22, 2019

(87) PCT Pub. No.: WO2018/154042
PCT Pub. Date: Aug. 30, 2018

(65) Prior Publication Data
US 2020/0230497 A1    Jul. 23, 2020

(30) Foreign Application Priority Data
Feb. 27, 2017    (ES) ................................ ES201730256

(51) Int. Cl.
*A63F 13/285*    (2014.01)
*A61N 1/04*    (2006.01)
(Continued)

(52) U.S. Cl.
CPC .......... *A63F 13/285* (2014.09); *A61N 1/0484* (2013.01); *A61N 1/36003* (2013.01); *G06F 3/016* (2013.01)

(58) Field of Classification Search
None
See application file for complete search history.

(56) References Cited

U.S. PATENT DOCUMENTS 5,572,248 A * 11/1996 Allen ...................... H04M 3/56
348/14.1
8,475,172 B2 * 7/2013 Lieberman ........... G09B 19/003
434/258
(Continued)

FOREIGN PATENT DOCUMENTS

CN    104706499 A    6/2015
EP     3127526 A1    2/2017

OTHER PUBLICATIONS

International Search Report and Written Opinion, PCT/EP2018/054480, dated Apr. 25, 2018.

*Primary Examiner* — Jason A Pringle-Parker
(74) *Attorney, Agent, or Firm* — Entralta P.C.; James F. Fleming; Peter D. Weinstein

(57) ABSTRACT

Examples relate to a system to apply stimuli to a human body. The system comprises a three dimensional display, a stimulation element, a specific piece of clothing, a portable background and a controller. The controller comprises a processor, data storage and an instruction set. The instruction set is to cooperate with the processor, data storage, three dimensional display and stimulation element to display a recorded three dimensional representation of an actor in movement and to transmit to the stimulation element stimuli synchronized with the movement. The actor is wearing a piece of clothing having the same aspect as the specific piece of clothing, the actor being located in front of a background having the same aspect as the portable background, the recording being from the actor point of view.

12 Claims, 4 Drawing Sheets

(51) Int. Cl.
*A61N 1/36* (2006.01)
*G06F 3/01* (2006.01)

(56) References Cited

U.S. PATENT DOCUMENTS

| | | | |
|---|---|---|---|
| 2006/0195042 A1 | 8/2006 | Flaherty | |
| 2009/0253109 A1* | 10/2009 | Anvari | G09B 23/28 |
| | | | 434/262 |
| 2012/0291020 A1* | 11/2012 | Scharer, III | H04N 5/272 |
| | | | 717/172 |
| 2013/0035734 A1 | 2/2013 | Soler Fernandez et al. | |
| 2014/0063177 A1* | 3/2014 | Tian | H04N 7/152 |
| | | | 348/14.07 |
| 2014/0070957 A1* | 3/2014 | Longinotti-Buitoni | ...... |
| | | | G06F 3/011 |
| | | | 340/870.01 |
| 2015/0077234 A1* | 3/2015 | Fullam | H05K 1/18 |
| | | | 340/407.1 |
| 2015/0317910 A1* | 11/2015 | Daniels | G09B 21/00 |
| | | | 84/485 R |
| 2016/0258181 A1* | 9/2016 | Jorba | E04H 15/22 |

\* cited by examiner

DISPLAY OF A THREE DIMENSIONAL RECORDING IN A SYSTEM FOR REHABILITATION

BACKGROUND

Some systems display a three dimensional recording to a human in relationship with a physical activity. Such system may give to the human the impression that such physical activity is practiced in the environment corresponding to the recording instead of the environment in which the human is actually placed. Such systems find an application for example when practicing games or sports and are aimed at providing the impression of practicing the game or sport in a pleasing environment different from the real environment.

BRIEF DESCRIPTION OF THE DRAWINGS

Various example features will be apparent from the detailed description which follows, taken in conjunction with the accompanying drawings, wherein.

DETAILED DESCRIPTION

Figure 1:
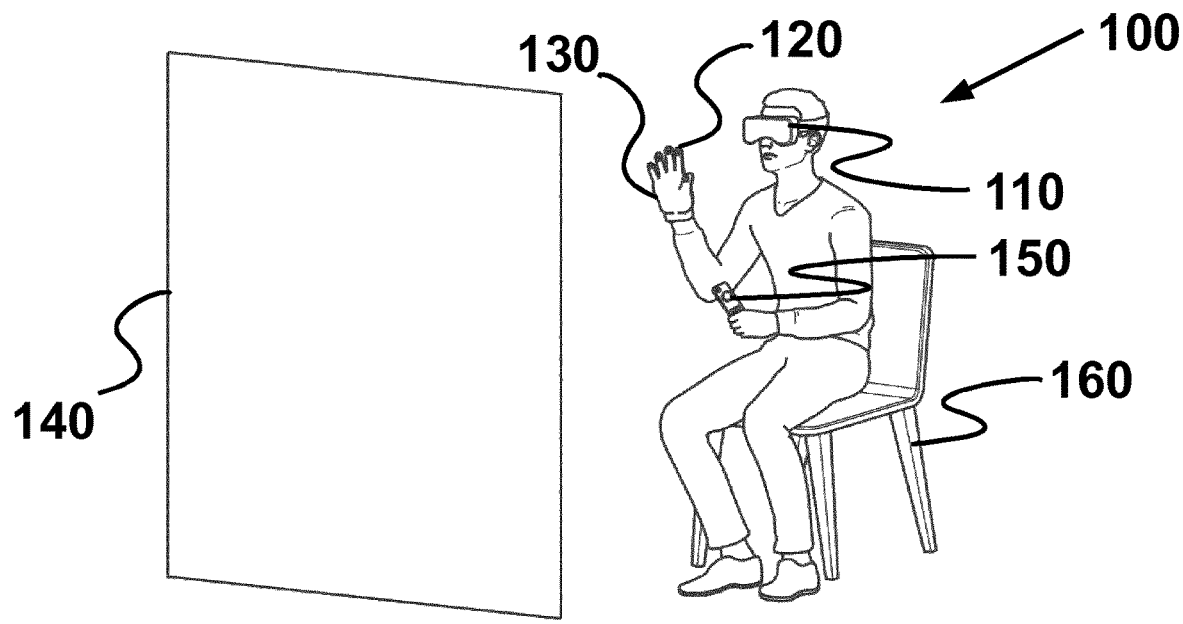
FIG. 1 is a schematic representation of an example system according to the present disclosure.

In an example, the present disclosure aims at applying stimuli to a human body synchronized with a movement, so the human body associates the stimuli to the movement it is synchronized with. In an example, the movement is a movement which this human body has difficulties to reproduce or even cannot reproduce. In an example, such difficulty or hindrance is due to a relatively long term immobilization of a body part, for example due to a fracture, or to some degree of damage to a part of the nervous system such as spinal cord damage. If the nervous system has somehow "forgotten" to practice a movement, an aim of the present disclosure may be to create for the nervous system the "illusion" that the movement is taking place. This "illusion" takes place using a three dimensional display. Reproducing such an "illusion" may allow learning how to reproduce this movement again, or even learn the movement if it never had been learned before (such as learning a new movement for a sport), or improve such a movement. It has been surprising to note that such "illusion" was more effective if the actual real surroundings of the human were corresponding to the surroundings of a corresponding three dimensional recording of the same movement by an actor. Indeed, instead of reproducing in the recording a pleasing environment related to an activity (for example, reproducing a ski slope in a mountain to practice a movement which an actor represents while skiing) it was surprisingly more efficient and effective to display a recording in which the environment was corresponding to the real environment in which the human is located when practicing the present disclosure. For example, if the human is located in a hotel room and practices a movement according to this disclosure, the nervous system of the human will perceive the movement better if the three dimensional representation corresponds to the appearance of the hotel room (and not to a ski slope). Without wishing to be bound by theory, it is believed that the central nervous system, because it actually knows that it is in a specific location such as a hotel room for example, will not be "fooled" or be as sensitive to a recording made in a place having a different aspect, such as a ski slope for example. One should mention that the three dimensional recording represents an actor in movement, such that the perception is that the movement takes place as reproduced by the actor, even if the movement is not reproduced by the human like it is by the actor, or even if it is not reproduced by the human at all. A possibility, in order to increase the perception of the nervous system, is to record the three dimensional representation in the same exact place as the one where the human will be practicing. It is however very costly and time consuming to prepare such recordings, and to customize them to a specific environment every time. This seemingly complex and costly customization procedure is resolved elegantly and in a surprisingly economical manner by providing a portable background and by having the actor located in front of a background having the same aspect as the portable background when making the recording. In the example of the hotel room mentioned above, the human being may set up or have the portable background set up to practice according to the disclosure. Because the recording will have been done with a background having the same aspect, the impression will be that that the three dimensional representation is of the actual human being practicing according to the disclosure instead of the actor. It is indeed an object of this disclosure that the human practicing according to the disclosure have the impression or sensation that they are themselves moving and do not realize that the movement which they observe with the three dimensional display is the one recorded by the actor but believe that it is their own movement which they are observing, even if this is an illusion facilitated by this disclosure. In an example, the portable background is very simple, such as a bed sheet or curtain hung in front of the human being for example, as long as such bed sheet or curtain has the same aspect as the one appearing as background on the three dimensional recording.

In FIG. 1, an example system 101 according to this disclosure is represented. The system 101 is to apply stimuli to a human body. In an example, the stimuli are of a mechanical nature, for example a vibration. In another example, the stimuli are electrical. In another example, the stimuli are magnetic.

The system 101 comprises a three dimensional display 110. In this example, three dimensional display 110 is provided by three dimensional goggles or glasses, for example goggles on which a mobile phone may be placed or glasses having integrated screens, one for each eye, in order to provide a three dimensional experience. In an example, the three dimensional display provides to each eye of the human a slightly different image of the same representation, the difference between the image seen by one eye and the image seen by the other eye producing the illusion of a three dimensional representation.

System 101 comprises a stimulation element 120. Stimulation element 120 is comprised in a glove. Stimulation element 120 comprises mechanical stimulation elements associated to each finger and to the palm of a hand. In an example, the stimulation element comprises a vibrating element, the stimuli comprising a vibration. In an example, the stimulation element comprises an electrical element, the stimuli comprising an electrical signal. In this example, stimulation element 120 is equipped with a wireless receptor allowing a communication with a controller 150. In an example, communication between a stimulation element and a controller takes place through wires. In an example, the stimulation element is a bracelet which may be placed on part of a limb. The stimulation element may transmit for example a vibration or an electrical field or a magnetic field. The stimulation element may be comprised in a wearable element, for example comprised in a piece of clothing.

System 101 comprises a specific piece of clothing 130. Specific piece of clothing 130 is a glove. In another example, the glove covers not only the hand but also the arm of the human. In an example, the specific piece of closing is in the field of vision of the human. In an example, the specific piece of clothing is covering at least part of a body part or of a limb of the human, the body part or limb being the body part of limb in movement in the recorded three dimensional representation of an actor. In an example, the specific piece of clothing comprises trousers. In an example, the specific piece of clothing comprises a vest. In an example, the specific piece of clothing comprises trousers and a vest. One should note that the actor in the recorded three dimensional representation wears a piece of clothing having the same aspect as the specific piece of clothing. This was surprisingly more effective in contributing to conveying to the nervous system of the human the illusion that the human was actually performing the same movement as the movement performed by the actor. In an example, pieces of clothing having the same aspect comprise pieces of clothing made from the same material. In an example, pieces of clothing having the same aspect comprise pieces of clothing of the same color. In an example, pieces of clothing having the same aspect comprise pieces of clothing of the same texture. In an example, pieces of clothing having the same aspect comprise pieces of clothing of the same size. In an example, pieces of clothing having the same aspect comprise pieces of clothing of the same shape. In an example, pieces of clothing having the same aspect comprises pieces of clothing having in common any one or more of their material, color, shape, size or texture. In the example of FIG. 1, the human may wear one or more pieces of clothing differing from the pieces of clothing worn by the actor, for example one or more pieces of clothing which may not appear in the field of vision of the human as he or she practices according to the disclosure of the invention.

System 101 comprises a portable background 140. Portable background 140 is a bedsheet, held up by a structure which is not represented. In an example, the portable background is a curtain. In an example, the portable background is a tent. In an example, the portable background covers more than 1 square meters in front of the human. In an example, the portable background covers more than 2 square meters in front of the human. In an example, the portable background comprises an area in front of the human and an area on top of the human. In an example, the portable background comprises an area in front of the human and an area on a side of the human. In an example, the portable background comprises an area below the human. In an example, the portable background comprises an area in front of the human, and an area on top of the human and an area on a side of the human. In an example, the portable background covers more than 4 square meters. In an example, the portable background weighs less than 20 kilograms. In an example, the portable background weighs less than 15 kilograms. In an example, the portable background weighs less than 5 kilograms. In an example, the portable background may be folded or arranged to occupy less than 0.5 cubic meter. In an example, the portable background may be folded or arranged to occupy less than 0.3 cubic meter. In an example, the portable background may be folded or arranged to occupy less than 0.1 cubic meter. One should note that the actor in the recorded three dimensional representation is located in front of a background having the same aspect as the portable background. This was surprisingly more effective in contributing to conveying to the nervous system of the human the illusion that the human was actually performing the same movement as the movement performed by the actor. In an example, portable backgrounds having the same aspect comprises portable backgrounds made from the same material. In an example, portable backgrounds having the same aspect comprises portable backgrounds of the same color. In an example, portable backgrounds having the same aspect comprises portable backgrounds of the same texture. In an example, portable backgrounds having the same aspect comprises portable backgrounds of the same size. In an example, portable backgrounds having the same aspect comprises portable backgrounds of the same shape. In an example, portable backgrounds having the same aspect comprises portable backgrounds having in common any one or more of their material, color, shape, size or texture. In an example, the portable background comprises pleasing figures, drawings or colors which can have a positive influence on the human.

System 101 comprises controller 150. Controller 150 comprises a processor, data storage and an instruction set. In an example, the controller is comprised in a mobile terminal such as a mobile phone or a tablet. In an example, the controller is comprised in a desktop or notebook computer. In an example, the controller is included in a server. In an example the processor performs operations on data. In an example, the processor is an application specific processor. The processor may also be a central processing unit. In an example, the processor comprises an electronic logic circuit or core and a plurality of input and output pins for transmitting and receiving data. In an example, data storage comprises one or more of volatile or non-volatile memory. Data storage may include any electronic, magnetic, optical, or other physical storage device that stores executable instructions. Data storage may be, for example, Random Access Memory (RAM), an Electrically-Erasable Programmable Read-Only Memory (EEPROM), a storage drive, an optical disk, and the like. Data storage is coupled to the processor. The controller comprises an instruction set. Instruction set cooperates with the processor and the data storage. In the example, instruction set comprises executable instructions for the processor, the executable instructions being encoded in the data storage.

While in this example the controller 150 is in the hand of the human, in other example the controller is not handled by the human. In some examples, the controller is not handled by the human in order to avoid or reduce distractions and increase focus on the movement according to this disclosure. In some examples, the controller is hanging from a necklace or from a bracelet.

The instruction set is to cooperate with the processor, data storage, three dimensional display and stimulation element to display a recorded three dimensional representation of an actor in movement and to transmit to the stimulation element stimuli synchronized with the movement, the actor wearing a piece of clothing having the same aspect as the specific piece of clothing, the actor being located in front of a background having the same aspect as the portable background, the recording being from the actor point of view. This combination of feature was surprisingly successful at transmitting to the human the illusion of being in movement in the same manner as the actor on the representation. This combination comprises the recording being from the actor point of view. Recording from the actor point of view means that the recording reproduces the surroundings of the actor as the actor sees them. In an example, the recording comprises a visual representation of a limb or body part of the actor in movement. Recording may be prepared using a video camera a set of video cameras held on the forehead of the actor. Recording may be prepared using a camera or a set of cameras comprised in glasses or goggles worn by the actor. In an example, the actor is of the same sex as the human practising according to this disclosure. In an example, the instruction set is to provide alternative recorded three dimensional representations in function of one or more of gender, race, age, weight, size or corpulence. Such alternatives may further improve the possibility for the human to identify the recording with reality by assimilating the appearance of the actor with their own.

System 101 comprises a body support structure 160. In this example, the body support structure is a chair. In an example, the body support structure is a bed. In an example, the body support structure comprises a harness. In an example, the body support structure is a walking frame. The body support structure may for example be used to avoid that the human would become tired, or to hold the human in a position appropriate for practicing the movement, or if the human would not be capable to maintain a position without a support structure.

Figure 2:
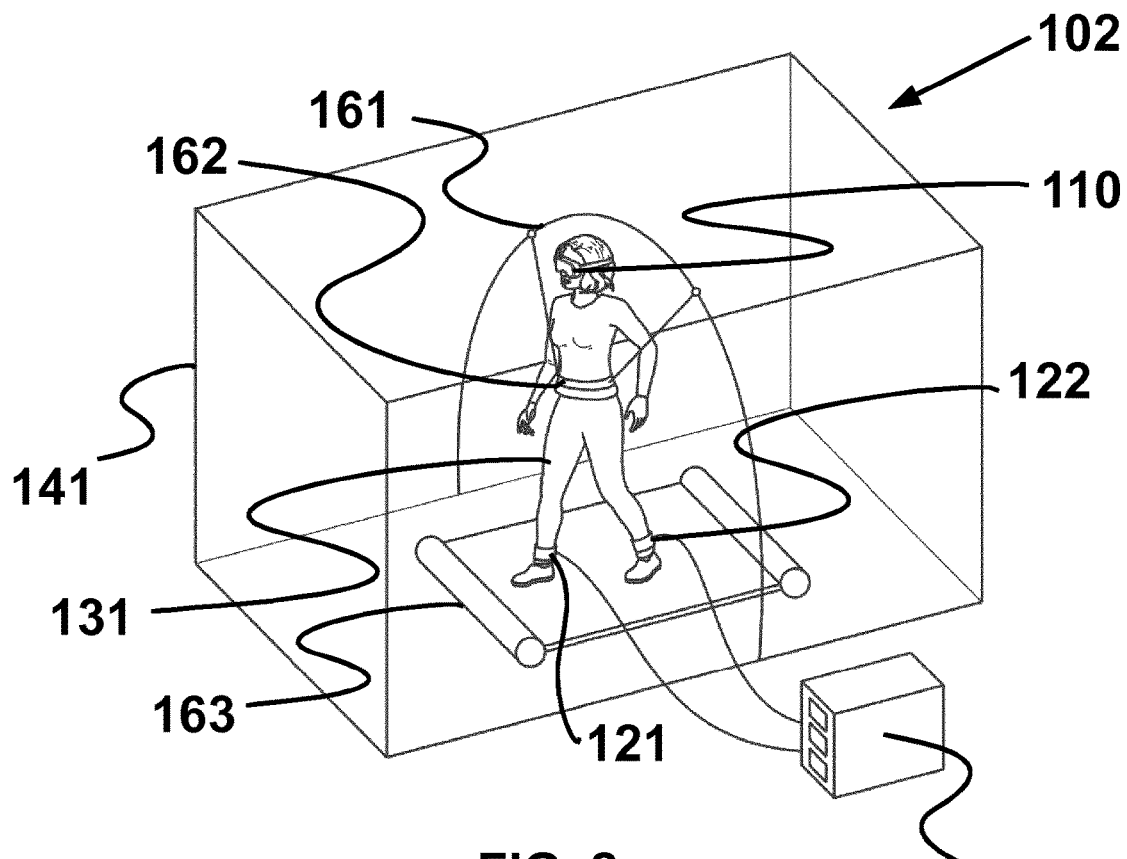
FIG. 2 is a schematic representation of another example system according to the present disclosure.

In FIG. 2, another system 102 according to the disclosure is represented. System 102 comprises the same glasses or goggles 110 as in system 101. System 102 comprises a stimulation element 121 located around a first ankle of the human being and another stimulation element 122 located around a second ankle of the human being. Stimulation element 121 and stimulation element 122 are in direct contact with the skin of the human. In another example, the stimulation element is applied with pressure against a body part of limb of the human. In another example, the stimulation element is separated from the skin of a human by a layer of textile. System 102 comprises a specific piece of clothing 131. Specific piece of clothing 131 comprises trousers. Such trousers have the same aspect as trousers worn by the actor in the representation displayed through glasses 110 such that when looking down towards the feet the human has the illusion to be looking at their own legs and do not realize that the legs are the legs of the actor. In an example, the specific piece of clothing comprises trousers and trainers or another type of shoe in order to further improve the illusion. The system 102 comprises portable background 141. Portable background 141 has a cubical shape comprising 6 sides and is a tent like structure comprising textile and poles, the poles holding the textile so the textile builds the walls of the tent. In an example, one or more side of the tent may be open, for example to render the structure lighter. System 102 comprises controller 151. In this example, controller 151 is a desktop PC. In this example, the controller communicates with the stimulation elements via wires. The controller may communicate with the glasses or goggles 110 in a wireless manner. System 102 also comprises a body support structure. The body support structure comprises a surrounding structure 161 on which a harness 162 is hung. Harness 162 may provide support to the human. System 102 further comprises treadmill 163. One may appreciate that in an example the human is not capable of controlling lower limbs and may be held by the harness 162 and be standing on the treadmill 163 without the treadmill being activated. In an example, the body support structure comprises elements also comprised in the recording. In an example, the treadmill is also present in the recording.

Figure 3:
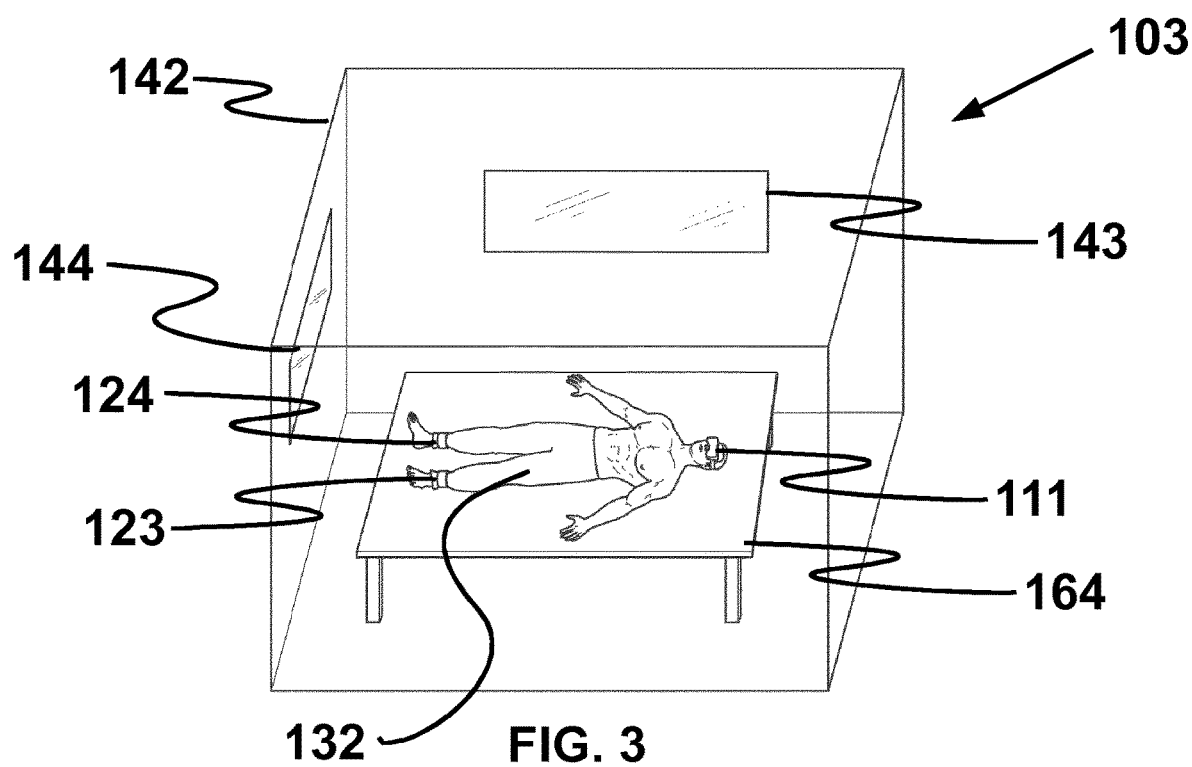
FIG. 3 is a schematic representation of a further example system according to the present disclosure.

In FIG. 3, another system 103 according to the disclosure is represented. System 103 comprises the glasses or goggles 111 as three dimensional display. In this example, glasses 111 comprise the controller, which transmits stimuli in a wireless manner to stimulation elements 123 and 124. In this example, the specific piece of clothing 132 comprises trousers. In this example, portable background 142 is a tent like portable background similar to the portable background 141 of FIG. 2. Portable background 142 comprises mirrors 143 and 144. Such mirrors allow increasing the perception of movement for the human, bearing in mind that the human does not actually see the mirrors but a representation of mirrors having the same aspect and being displayed in the recording. System 103 also comprises a body support structure. The body support structure comprises a surrounding a bed like structure 164 on which the human is lying.

In an example, the movement comprises a movement of lower body limbs of the actor, for example a leg or a foot. In an example, the movement comprises a movement of top body limbs of the actor, for example an arm or a hand. In an example, the movement comprises a movement of both lower and top body limbs of the actor. In an example, the movement comprises a movement of the hips of the actor.

Figure 4:
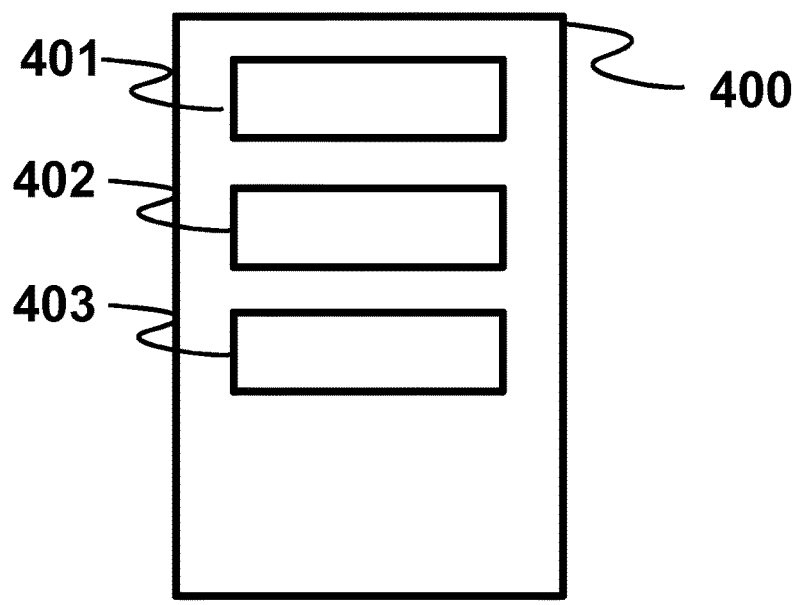
FIG. 4 is a schematic representation of an example non-transitory machine-readable storage medium according to the present disclosure.

FIG. 4 illustrates an example of a non-transitory machine-readable storage medium 400 encoded with instructions executable by a processor, the machine-readable storage medium comprising instructions 401 to detect a selected body movement; instructions 402 to display a three dimensional recording of the selected body movement, the three dimensional recording being from an actor point of view and representing the actor facing a portable background; and instructions 403 to transmit stimuli synchronized with the movement. In an example, instructions are provided to generate a stimuli, for example using a stimulation generation module which may be comprised in an example system of this disclosure. In an example, the storage medium further comprises instructions to display a selection of different body movements. In an example, a machine-readable storage medium according to this disclosure is implemented in the controller of a system according to this disclosure. In an example, the selection of body movements comprises selecting one or more of gender, race, age, weight, size or corpulence. In an example, the selection of body movements comprises selecting one or more of a movement strength, amplitude or frequency. In an example, the selection of body movements comprises selecting one or more of a leg, arm, hand, foot, hip, elbow, finger, fore arm, fore leg, neck, back, lower back, lower neck, ankle, wrist or palm. One should note that the transmission of stimuli may be provided to a stimulation element of a system according to this disclosure associated to any member of body part corresponding to such movements.

Figure 5:
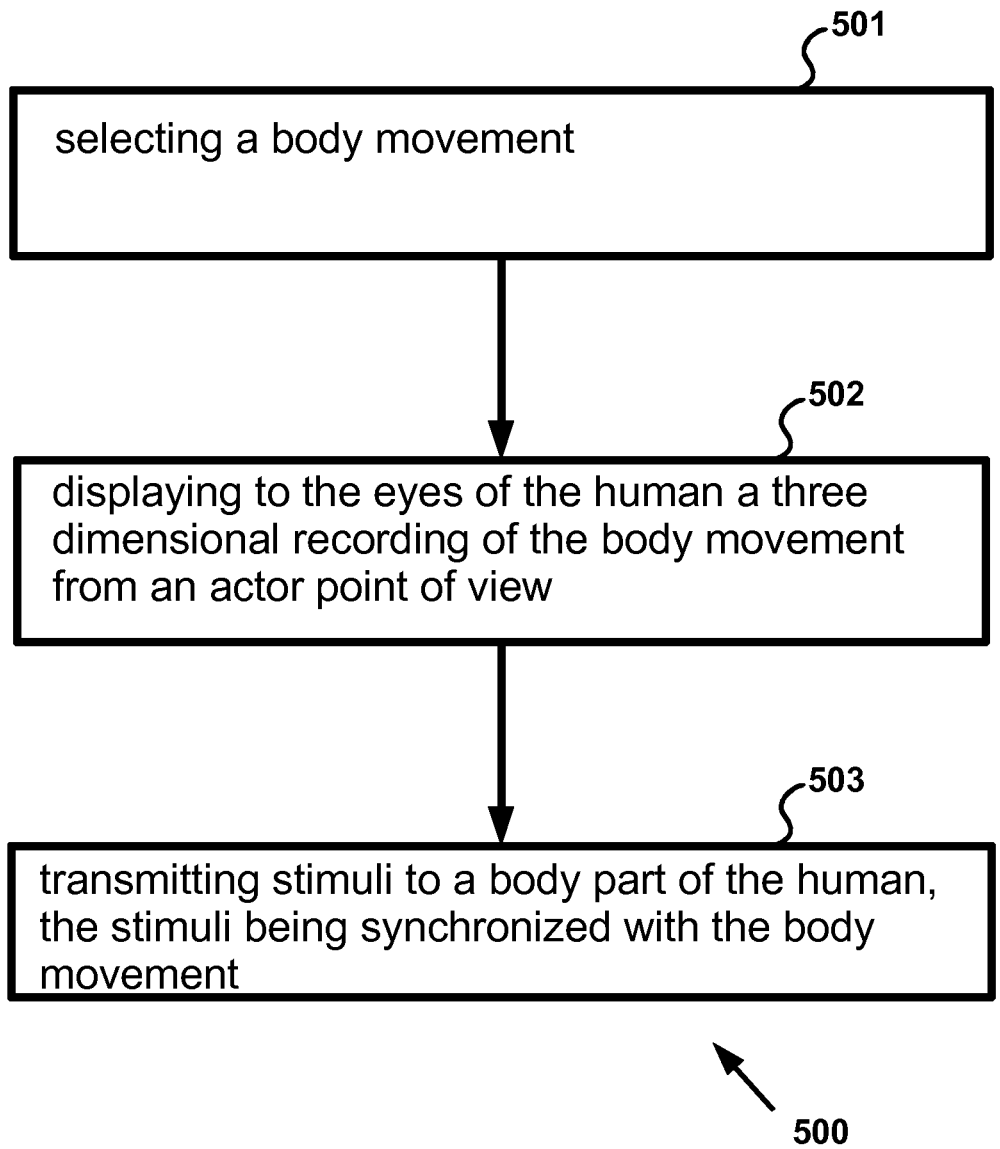
FIG. 5 is a block diagram representation of an example method to apply stimuli to a human according to the present disclosure.

FIG. 5 illustrates an example of a method 500 to apply stimuli to a human according to this disclosure. The method comprising selecting a body movement in block 501; displaying to the eyes of the human a three dimensional recording of the body movement from an actor point of view in block 502; and transmitting stimuli to a body part of the human, the stimuli being synchronized with the body movement in block 503; whereby the actor is wearing a piece of clothing having the same aspect as a specific piece of clothing worn by the human, and the human is facing a portable background having the same aspect as the background facing the actor in the recording. In an example, the stimuli are generated by the system of this disclosure, the method including generating the stimuli. In an example, the method comprises moving the body part of the human according to the selected movement, which may apply if the human is not capable of directing the movement independently, in which case external help in making the movement may contribute in a rehabilitation process. In an example, the method includes playing a voice recording describing the body movement of the human, such verbalization being for example encouraging the human in the process, or to describe the movement to the human in order to promote having the human anticipating or assimilating the movement, thereby further contributing to the object of this disclosure. The verbalization may also be provided live by an external operator, for example an operator who also would provide external help in moving the body part according to the selected body movement.

In an example, the present disclosure relates to a neuro-rehabilitation system that is based on the synchronization of nerve efference (related to efferent nerves) with functional and sensitive afference (related to afferent nerves), favoring the mechanisms of plasticity and synaptogenesis, as well as re-learning in the motor control.

In examples, this disclosure relates to areas other than neuro-rehabilitation. Such other areas may comprise neuromuscular training and rehabilitation, may apply to maintaining or fomenting trofism, sensitivity or motor control aspects, for example by the nervous and muscular synchronization by stimuli of this disclosure, at the motor and proprioceptive levels. Other areas of application would comprise, in a non-limiting manner, issues due to an immobilization of part or all of a human body, for example with a neurological cause (for example an ictus, seizure, fit, spinal cord injury, sclerosis, multiple sclerosis), a mechanical cause (for example fracture, dislocation, sprains, ligament or articulation injury) or other causes such as, in a non limiting manner, age, weakness, recovery following a medical intervention or long term rest. Other areas may comprise atrophy, treatment of pain such as for example caused by arthrosys, arthritis or amputation.

An object of this disclosure may be to achieve controlled work at acute stages of an injury, as well as enable intensity in repetition and provide controlled motor reorganization work, both in terms of activation and sequencing (spatial and time order of a stimulation and related contraction).

As such, this may be a neuro-rehabilitation system that, with respect to the cortical-pyramidal origin in the nerve efference, may allow for modulated physical (motor and proprioceptive) feedback, leading to neurological and muscular synchrony, and thus making it possible to have guided work in terms of plasticity.

Neuro-rehabilitation is the field of rehabilitation specialized in the treatment of injuries to the nervous system. Such field is for example associated with mobility issues. Neurological pathology results in one or several physical or cognitive dysfunctions that produce high rates of disability. Basic functions of daily life such as walking, eating, talking, using the bathroom or going out with friends can become actions that cannot be carried out. Thus, there are as many neuro-rehabilitation techniques and as many specialists within its competence as possible dysfunctions, including experts in walking, language, attention and memory and training in daily life. Doctors, physical therapists, speech therapists, occupational therapists, psychologists, social workers, teachers and educators are the professionals who surround a person who suffers a neurological injury.

Neuro-rehabilitation works with different techniques, each one based on different assumptions and methodologies. However, the principle that may follow the rehabilitation of an injury to the central or peripheral nervous system is based on the plastic capacity thereof. This plastic capacity may be correctly oriented to achieve the correct reorganization of the circuit, neuronal and glial modulation and axon growth, thus increasing chances of achieving recovery.

This disclosure may offer an improved plasticity; in other words, treatments that may enable the circuits to be correctly modeled and the creation of neuronal connections to subsequently (or simultaneously) may be strengthened by physical means of rehabilitation.

The system of this disclosure may be considered a work tool based on nerve signal-muscular contraction synchrony, such that said nerve signal originates from mechanisms of imitative observation favored through a very specific viewing and immersion system.

Furthermore, an electrical or mechanical feedback of the corresponding stimulation element may be programmed and modulated to provide a nerve and contractile work that a human with a specific injury may carry out.

More specifically, a system according to this disclosure may apply an interaction between different blocks which provide a sensory input (visual efference) and a stimulation signal of interest "(for example mechanical, electrical or magnetic) at the output (contractile and proprioceptive afference), based on the commands established by a control process.

In an example, the system comprises virtual reality glasses, a recording and a stimulation element to generate via a controller a pattern of excitement to be executed by the stimulation element.

Virtual reality or three dimensional glasses may be a specific support (VR glasses) together with a portable terminal such as a cell phone equipped for example with an Android operating system, with a screen for example between 5 and 6 inches in diagonal (about 12 to 15 cm) and a resolution of for example 1920×1080 or 4K or higher resolutions. A recording may be stored in the portable terminal at the highest quality supported by the portable terminal. This portable terminal may be placed on virtual reality glasses. Recordings indicated for a human may be chosen and viewed through an application.

The projection of a scene of interest based on an example system may be carried out, allowing the patient to be immersed in the context of the action carried out (in first person). A projection of the recording via video may be based on the grounds of excitement of the system of motor mirror neurons, obtaining greater recruitment in the excitement of motor neurons which may provide the cortical-spinal origin of the nerve signal.

A recording, which may show an activity, may be based on a stereoscopic projection recorded in 360° of a movement, observed from the first person perspective (or point of view) and intending to be a movement made by the very observer. This technique may be based on the recording of the true environment by means of the separate capture of each eye of an actor, respecting the interocular distance in order to acquire an immersive experience in which the human may be able to feel the depth of the image generated by stereoscopy. The actions may be verbalized prior to their execution. The quality of the immersion is ensured with the attainment of the depth explained above and given adequate image resolution. Such quality of immersion is permitted by including in the recording a portable background having the same aspect as the portable background of the system.

In an example the stimulation may take place using an electro-stimulator, for example wirelessly connected to virtual reality glasses and a cell phone, the cell phone being a portable terminal that enables the electrical signals to be applied with the appropriate parameters for the rehabilitative process, facilitating the completion of two tasks, one consisting of measuring the neuromuscular activity of the human or patient in order to determine whether to apply electro-stimulation, and the other corresponding to a synthesis of the rehabilitative electrical signal to be applied to the human or patient. The rehabilitative electrical signal applied once a predetermined threshold of the measured neuromuscular activity is exceeded belongs to a specific rehabilitation program according to a pathology to be treated.

In an example, the electrical or mechanical stimulator is comprised in the stimulating element of the system of this disclosure, whereby:
 the application of the electro-stimulation is guided (generation of potentially rehabilitative waveforms);
 the neuromuscular activity is registered during the viewing of a three dimensional video recording;
 if the neuromuscular activity exceeds a pre-established threshold, electrical or mechanical stimulation occurs (said stimulation triggers electrical or mechanical pulses that produce contraction feedback and make it possible to train the increase of the muscular recruitment, synchronized with the cortical-nerve origin achieved through virtual reality);
 the exercise is registered, making it possible to verify and modify it and make progress with proposed therapeutic objectives.

In an example the electrical or mechanical stimulator may be an input/output element for both control signals and system signals; in other words, it may be a device for obtaining control signals and a device for synthesizing and applying stimulation signals.

Problems that may be solved by means of a system of the disclosure correspond for example to:
 Problems originating from the nerve signal: The system may begin the work by stimulating the premotor cortical regions. The time sequence in the activation of the pyramidal tract starts in these regions. The neuronal mechanisms of anticipation and, in this specific case, of imitation, reside in these areas and enable the motor neurons of these regions to develop strong direct connections with the entire pyramidal tract. The intention of movement leads to the synaptic firing of these regions to the pyramidal tract and marrow. These visual-motor neurons that bring together motor anticipation and execution are those called mirror neurons. The excitement/participation thereof to make a controlled voluntary movement may take place. The way of providing this excitement is through an immersion device (virtual reality) that encourages observation with imitative intention. The display is carried out such that a high excitement of the motor mirror neurons responsible for motor imitation/anticipation is used.
 Problem of the motor target: The system records the proper reception of the nerve signal through monitoring with an electromyogram. Thus, the target of the signal on the muscle that the human intends to move may be controlled.
 Problem of plasticity: The system may enable the use of appropriate circuits, since the origin and end of the nerve signal associated with the action carried out by the patient may be controlled. Furthermore, it may favor the creation of axons and connections thereof, since it may be a multidirectional circuit, where the nerve signal may not travel in a single direction, but rather it may enable synaptic consolidation work, and it also may offer an electrical or mechanical input that may work on nerve conduction in terms of myelination or rehabilitation of motor capabilities of a body or body part.

In an example, one may carry out an analysis of the sequence of movements of a self-immersive video recording that may record a specific motor action that is verbalized for example about one second earlier, carried out by an individual or actor (a real, non-virtual action) with a first person perspective or actor point of view and within an environment void of distractors, for the subsequent time synchronization thereof with the electro-stimulator, in the presence of a portable background having the same aspect as the portable background of the system. An output may be data for the development of a rehabilitation program (data on execution periods and moments of the sequence of movements of the video that the system will reproduce).

An example of a method of the disclosure may include:
 applying to the patient or human the stimulation element (for example electrodes of an electro-stimulator) in the anatomical area of interest (on the motor point of the muscle of interest).
 selecting the recording or video that contains the recording of the activity or movement to be reproduced (upper member or limb or lower member or limb for example)
 selecting a program to be applied, which may contain guidelines for activating the stimuli, for example based on a pattern of movements contained in the video or recording and the time sequencing thereof. This selection may be carried out based on the data that the patient or human introduces into the system (cascade of characteristics such as age, gender, size, or weight for example).
 measuring the patient's or human's neuromuscular threshold (average of three analytical contractions of 5 seconds each for example). Setting the threshold for work during the session.
 The patient or human may put on the virtual reality glasses or three dimensional display, made up for example of a physical support and lenses and an element onto which the video or recording will be projected (cell phone for example).
 playing or reproducing simultaneously the recording or video and the stimuli, where the link of synchronization is the system controller, which orders the discharge of electrical or mechanical stimuli synchronized with the viewed action or movement, provided that feedback has been detected by the patient or human upon observing the action; in other words, having exceeded the predetermined threshold of the active muscular activity.
 recording the session, including:
The program which has been applied
The cascade of characteristics that have led to the selection of this program
The activation threshold considered
The video that has been projected
The neuromuscular activity associated with the session.

In an example, the system allows synchronizing the reproduction of an immersive video or three dimensional recording by means of virtual reality with the application of stimuli in a coherent and synchronized way with the movements observed by the patient or human in the video or recording that is projected. In this way, the generation of mechanical (vibrating) or electrical waveforms will be produced, on one hand, in the moments in which it is determined that movement is being produced, based on the analysis of the video that records the movement; and on the other hand, when the analysis of the measuring step of, for example, an electro-stimulator (EMG) (when the stimulating element comprises an electro-stimulator) determines that there is neuromuscular activity that exceeds a pre-established threshold. Furthermore, the system may enable the automatic and smart selection of the program to be applied based on the characteristics of the patient or human (which are introduced for example manually or using the three dimensional display into the controller) and the recording in the data storage of the session carried out (program applied, activation threshold, video used, neuromuscular signal).

Thus, an example purpose of the system is, on one hand, to reproduce the immersive video by using virtual reality techniques and elements and, on the other hand, applying stimuli in a coherent and synchronized way with the movements observed by the patient or human in the video that is projected (neuromuscular synchrony).

The system of the disclosure may provide the following:
enables work in acute stages of an injury, leading to an intervention in chemical and structural post-injury mechanisms, making it possible to face the toxic and harmful mechanisms of plasticity that may occur during the first three months and that may trigger permanent dysfunction;
favor the work of positive plasticity, fighting the devastating mechanisms of poor compensation or loss;
anticipate correct subsequent/simultaneous physical work, working on correct learning consolidation;
enable the intensity of the therapy to be molded not only in terms of repetition, but also in terms of motor recruitment and the original nerve signal;
be coherent with current neuro-rehabilitation knowledge.
provide a virtual reality support designed to enable cortical and subcortical excitement involved in motor imitation and anticipation, achieving greater excitation of the cortical motor neurons and pyramidal tract to support the mechanisms of plasticity;
offer with the stimulation element a specific current type or vibration according to the state of the muscle, the anatomical area and the state of muscular innervation that the pathology of the human needs;
enables the patient's or human's evolution to be recorded, the training objectives to be set and the active nerve and muscular work of the user to be ensured;
provide a connecting link to achieve synchrony between voluntary muscular activation and electrical feedback as a positive and assistive reinforcement for the recovery work of muscular recruitment;
provide a portable technology that can be used as a tele-rehabilitation tool by facilitating the controlled repetition and monitoring of therapeutic performance.

Figure 6:
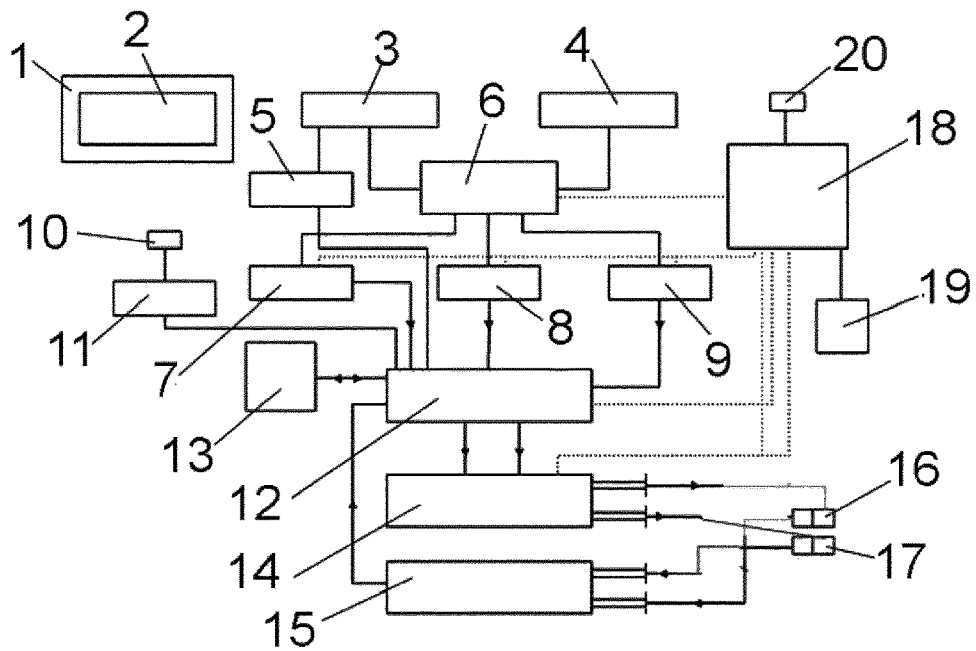
FIG. 6 shows a block diagram of an example system of the present disclosure.

FIG. 6 shows a block diagram of an example system of this disclosure, comprising virtual reality glasses as three dimensional display, a support for the cell phone used for the video presentation as three dimensional recording, and a stimulating element comprising an electro-stimulator with wireless connection with a controller.

Figure 7:
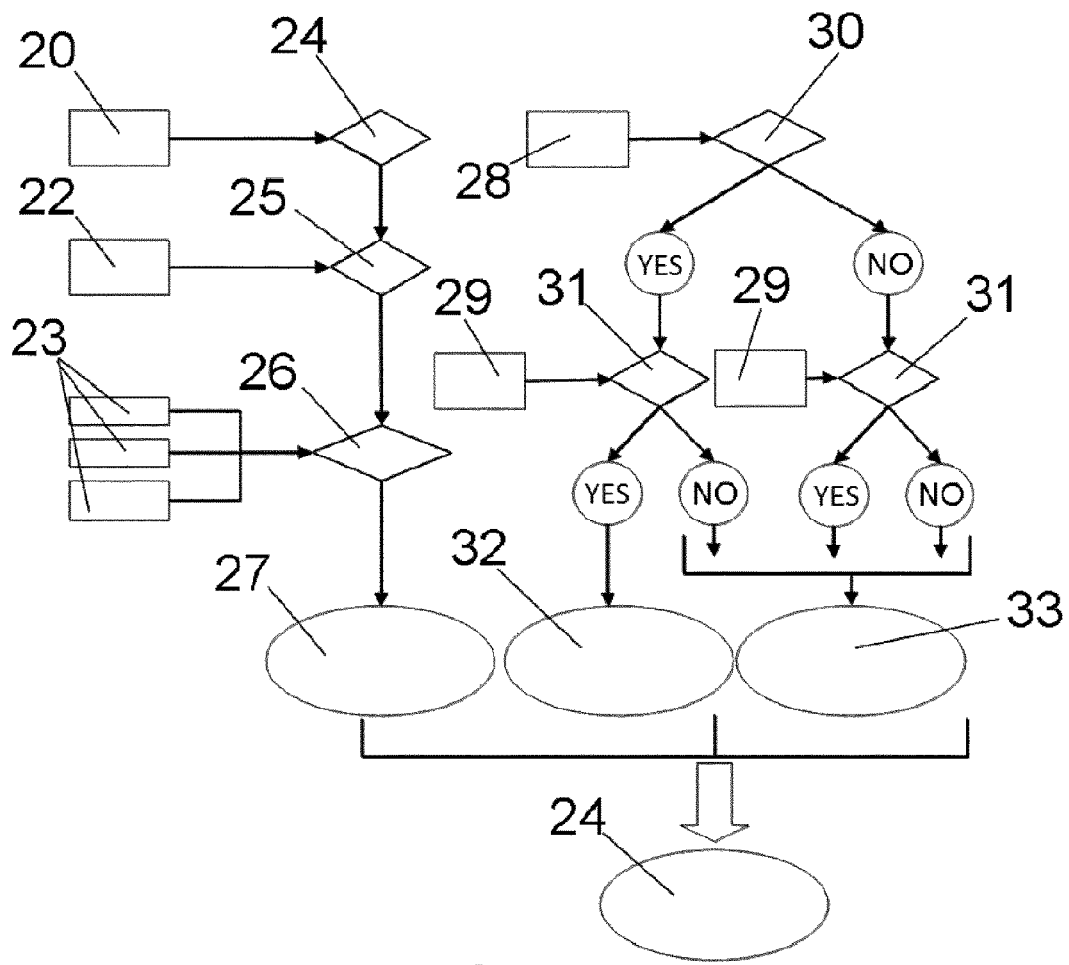
FIG. 7 shows an example flowchart related to the present disclosure.

FIG. 7 shows an example flowchart on the basis of which an electro-stimulation signal to be applied may be determined by a patient's or human's self-introduction of their physical characteristics related to the rehabilitation process (such as, for example, age, weight, muscular state, sensitivity and state of the skin).

FIG. 6 shows the VR (virtual Reality) support 1 or three dimensional display comprising the virtual reality glasses and the cell phone 2 as a reproduction element of the recorded video, such that the telephone includes the controller and wirelessly communicates with the electro-stimulator that constitutes the remaining blocks of the figure, enabling the individual to carry out rehabilitation in any environment without needing to use a separate computer. The lenses of the virtual reality glasses enable the patient to couple the optics of the video, leading to a perfect focus. The cell phone 2 that constitutes the reproduction device or projection support includes an Android device with a screen of between 5 and 6 inches and a screen resolution of 1920×1080 or more, such that videos indicated for each patient may be chosen and viewed through an application. Furthermore, by forming part of the electro-stimulator, the corresponding display 3, keypad 4, a control module 5 of the display, an external interface adaptor 6, from which the selection blocks of the program 7 are derived, the activation control block 8 and the SW loading block 9 are established, respectively, all being attached to a microprocessor 12 to which a communications module 11 and a Bluetooth module 10 are attached. The microprocessor 12 will have the corresponding memory or data storage 13 thereof, being attached to a pulse generator 14 and the electromyography device or EMG 15, the measurement of which corresponds to the level of the signal generated by the patient when they observe an action in the virtual reality projection system. The electro-stimulator includes a pair of electrodes 16 and 17 connected to the pulse generator 14 and the EMG 15. The electronics will be assisted by a power block and power control 18, attached to a battery 19 and a connector 20 for the recharging/rehabilitation thereof. By applying the electrodes 16 and 17 to the corresponding areas of interest, the signal resulting from the capacity of muscular contraction and the subsequent movement made by the patient can be determined, where it corresponds to obtaining the control signal (threshold of contraction capacity) by the EMG device 15, while when synthesizing and applying the stimulation signal, the electro-stimulator will generate electro-stimulation signals based on the wave type defined in the program selected, the time pattern established by the movements reflected in the video projected and the control signal that determines whether the signal agreed upon should be applied, since the activation threshold has been exceeded. In this way, the program selected will determine what type of signal is applied and the time video pattern will determine when the signal is applied, such that these two INPUTS, along with that which constitutes the control signal/exceedance of the activation threshold, are applied to the very electro-stimulator, said inputs being defined in the following way:

Example program selected/type of signal to be applied are described. In an example, the selection of the type of electro-stimulation signal or stimuli to be applied, product of the variables selected in the cascade of information that the patient introduces at the beginning of their rehabilitation session, is of relevance for the efficiency of the system and support in the rehabilitative process. The system enables the application of compatible and favorable waveforms of the rehabilitation processes. The parameters of the signals to be applied are included in the following table, obtained after reviewing multiple current clinical trials with high quality evidence:

In an example, the waveform and parameters of the signal to be applied will be given by the characteristics included in the table above.

In an example, the pulse generation module 14 is responsible for the synthesis and transmission of the electro-

|  | Shoulder subluxation | Clubfoot walk | Functional hand | Spasticity | Strengthening | Denervated muscles |
|---|---|---|---|---|---|---|
| Waveform | Asymmetric-Two-phase | Asymmetric-Two-phase | Asymmetric-Two-phase | Symmetric Asymmetric-Two-phase Russian | Symmetric Asymmetric-Two-phase Russian | Square or triangular single-phase |
| Pulse duration | 200-350 μs | 200-350 Ms | 200-350 μs | 250-500 μs | 200-700 μs | 1-450 ms (2nd motor neuron) 50-1000 μs (1st motor neuron) |
| Frequency | 30-40 Hz | 30-40 Hz | 30-40 Hz | 20-60 Hz | 30-85 Hz | 1-500 Hz |
| Amplitude | 3 s | 3+ | As low enough to operate | 3+ | Isometric maximum | Enough to obtain contraction |
| Ramp lifting time | 3 s | 0-1 s | 1 s | 2-3 s | 1-5 s | N/A |
| Ramp rest time | 3 s | 0-1 s | 1 s | 2-3 s | 1-2 s | N/A |
| Work system (duty cycle) | 1:5, 1:3 to 1:1 |  |  | 1.1 3:4 | 1:3-1:10 | 1:3-1:10 |
| Treatment/ session time | 30 min-6 h | Until fatigue | Until fatigue | 10-45 min | 20 min to 1 h/day | 30 min to 8 hours |
| No. sessions and weeks | 5-7 sessions/week 4-6 weeks | Until fatigue | Until fatigue | Reduced Ashworth variable | 3-5 session/week 4-8 weeks | From 4 days to 4 years |

Example Time pattern of the video or recording is described. In an example, the second input that will determine the application of the electro-stimulation signal is the time pattern of movement in the video. In a sequence, the recorded video will contain a series of movements made by the actor. During said sequence, the patient will execute (imitate) movements in determined time intervals. These intervals (start, duration, end) may be measured and the values obtained should be introduced in the software that will govern the operation of the system. Indeed, as a possible condition for the application of electro-stimulation, the video projected in a synchronized way should show an active movement of the anatomical area to be rehabilitated.

An example control signal of measurement of EMG and exceedance of the activation threshold is described. In an example, the third signal that determines the application of the electro-stimulation currents is based on the reading of the neuromuscular signal generated by the patient given the observation of a specific action. As a result of the properties of the mirror neurons, the simple observation of the action (respecting the fundamental factors in order to achieve the excitement thereof) will generate a motor response in the patient (motor resonance). If this motor response (imitative intention) exceeds a determined threshold measured by means of an EMG, the application of the electro-stimulation signal will be enabled.

In an example, taking into account the contribution of the three defined inputs, the electro-stimulation signal will be applied when the following occurs simultaneously:
 There is movement of the anatomical area in the video shown to the patient.
 The set activation threshold obtained through a previous request of voluntary contraction of a determined anatomical region is exceeded.

stimulation signal that will be applied to the patient. The specification of this module is given by the following parameters:

| PULSE GENERATION | |
|---|---|
| Number of channels | 2/4 |
| Signal amplitude | 0-160 mA - 500 Q |
| Waveform | Asymmetric two-phase, symmetric two-phase, Kotz, Square single-phase, Triangular single-phase |
| Pulse width | 1-600 ms (denervated muscles 2nd motor neuron) 100-900 μs (remaining cases) |
| Frequency | 1-500 Hz (denervated muscles) 10-100 Hz (remaining cases) |
| Ramp lifting time | 0.1-7 s |
| Ramp rest time | 0.1-7 s |

In an example, a series of programs (or selection of body movements) that will be associated to the circumstances of each individual patient after the fact is defined. These programs may define the parameters and characteristics of the electro-stimulation signals that will be generated on the basis of the table already discussed above.

In an example, the pulse generation block enables these programs to be defined. An example of a treatment program would be the following:

| PROGRAM 1 | |
| --- | --- |
| Signal Amplitude | 20 mA |
| Waveform | Asymmetric two-phase |
| Pulse width | 300 μs |
| Frequency | 40 Hz |
| Ramp lifting time | 1 s |
| Ramp rest time | 1 s |

The example electro-stimulator proposed enables the configuration of these programs based on each patient's needs and conditions. The selection of the program will be carried out automatically based on the information provided by the patient as an input from the device (variables of age, weight, muscular state, sensitivity and state of the skin).

The example sequence to determine the type of program that will be applied to the patent is defined in the flowchart corresponding to FIG. 7. The following can be identified in it:

As inputs 21, 22, 23, the different variables and conditions that define the patient's profile and determine the characteristics of the electro-stimulation signal that will be applied.

As an output, the electro-stimulation signal 24 to be applied, with characteristics according to the conditions, defined as inputs, of the patient.

A first group of variables (inputs) determines the following characteristics of the electro-stimulation signal (output):
  Frequency
  Pulse width
  Waveform
  Ramp times
  Other variables are:
  Age 24, numeric variable
  Weight 25, numeric variable
  Muscular state 26, with three possible Boolean variables (yes/no)
Spasticity
Atrophy
Denervated muscles The combination of the values obtained for these three variables may define the properties of the system output (electro-stimulation signal) that will be applied to the patient indicated above, specifically a first output 27, related to the frequency, pulse width, ramp times and waveform.

A second group of variables 28, 29 may determine the pulse amplitude 32 and whether it is necessary to limit it 33. These variables are:
  Normal sensitivity 30, Boolean variable.
  Good general state 31 of the area of the skin to which the electrodes are applied, Boolean variable.

The algorithm for selecting the signal of the software may calculate, on the basis of the inputs that the patient makes in the machine, the electro-stimulation signal (program or set of instructions) that should be applied. Thus, based on the patient's introduction of their age, weight, muscular state/pathology, state of skin and sensitivity, the controller may determine the electro-stimulation signal to be applied.

The capture block may provide establishing a threshold above which a discharge on the anatomic al area of the patient should or should not be carried out. It may be based on measurements taken from an electromyography system (EMG) of the neuromuscular signal level developed by the patient when they observe an action with an imitative intention in the virtual reality projection system.

The capture block may measure the neuromuscular parameters of the patient (EMG) and it will be provided as input to the controller of the system, constituting the control signal 3 defined previously and that will determine whether to apply electro-stimulation in real time.

The specification of this capture module is given for example by the following parameters:

| EMG | |
| --- | --- |
| Number of channels | 2 |
| Detection range | 0.4 to 1500 μV |
| Sensitivity | 0.2 μV |
| Frequency range | 1-500 Hz |
| Accuracy | <8% of the measurement |
| Rejection filter | 30 dB to 50 Hz (Spanish electricity grid) |

In the electro-stimulator, surface electromyography electrodes 16-17 that are for example flexible, hypoallergenic and disposable in sizes of 25×25, 40×40, 50×50 mm or 100×50 mm, according to the anatomical region to be stimulated, may also be used. They may be self-adhesive and able to be used repeatedly. When not used, the electrodes or stimulating element may be stored with a plastic protector. Allergic reactions to the adhesive of the electrodes may occur, even though they are hypoallergenic, in which case, the treatment should be interrupted.

Furthermore, the controller of the system may govern the operation thereof based on all the inputs detected and the system programming carried out, which may be based on the previous embodiment of videos in which actions or activities are reflected that the patient will be asked to reproduce simultaneously during viewing (imitation). The analysis of each video may lead to the creation of a data package associated with the activities, in which the moments and duration of the muscular activity may be collected.

Likewise, a method according to the invention may include an instruction to include a package for threshold exceedance, obtaining the measurement of recorded activity by means of the EMG device 15, comparing it to the required threshold and offering a value of "0" or "1" at the output, based on whether said threshold has been exceeded. Thus, a rehabilitative signal for each patient/pathology may be modulated by an activation signal, to thus generate a potentially rehabilitative signal that is applied coinciding with the moments in which there is movement in the video, provided that the activation threshold measured on the basis on the EMG device 15 is exceeded.

An example neuro-rehabilitation system may be based on establishing synchronization of nerve efference with contractile and proprioceptive afference, where the link of synchronization is a set of instructions stored on data storage and executed by a processor comprised in a controller, in that it comprises virtual reality glasses 1 constituting a support for a reproduction device, such as a cell phone 2 for example, with wireless connection, through the reproduction device of which determined videos or three dimensional recordings made according to the physiological principles of maximum excitement of the mirror neurons (real video and recorded with a background having the same aspect as a provided portable background according to this disclosure, first person perspective or point of view, analytical motor actions verbalized prior to their execution and an environment free of distractors) are chosen and viewed in the presence of the provided portable background; further comprising a portable stimulation element, for example an electro-stimulator, with wireless connection to the playback device or to the controller, provided with means for measuring neuromuscular activity of the patient, analyzed by the software, in order to determine whether to apply electro-stimulation to the patient and, on the other hand, to carry out a synthesis of the respective rehabilitative electrical signal to be applied to the patient, based on what is determined by that software from the cascade of variables previously selected by the patient, having envisaged that the respective electrical feedback of the electro-stimulator is programmed and modulated to provide the nerve and contractile work that the patient can/should be carry out and that aims to obtain support in the mechanisms of plasticity through nerve and muscular synchronization. Such neuro-rehabilitation system may be such that the electro-stimulator comprises a pulse generation module 14 responsible for the synthesis and transmission of the electro-stimulation signal that will be applied to the patient, and a capture module (EMG electromyography device) that enables a threshold to be established above which the discharge of said electro-stimulation signal should or should not be carried out on an anatomical area of the patient, being based on the measurement of the level of the neuromuscular signal developed by this patient, obtained from said electromyography device EMG 15. The neuro-rehabilitation system may be such that the electro-stimulator is complemented with two pairs of electrodes of electro-stimulation and electromyography 16-17 that receive the signal from a pulse generator 14, controlled by a microprocessor 12 for the application thereof to the patient, and in turn record the voluntary neuromuscular activity of the patient, sending said measurement to the electromyography device EMG 15.

The preceding description has been presented to illustrate and describe certain examples. Different sets of examples have been described; these may be applied individually or in combination, sometimes with a synergetic effect. This description is not intended to be exhaustive or to limit these principles to any precise form disclosed. Many modifications and variations are possible in light of the above teaching. It is to be understood that any feature described in relation to any one example may be used alone, or in combination with other features described, and may also be used in combination with any features of any other of the examples, or any combination of any other of the examples.

The invention claimed is:

1. A system to apply stimuli to a human body to mimic an activity for muscle training or rehabilitation, the system comprising:
 a three dimensional display;
 a stimulation element;
 a specific piece of clothing;
 a portable background; and
 a controller, the controller comprising a processor, a data storage and an instruction set, the instruction set to cooperate with the processor, the data storage, the three dimensional display and the stimulation element to display a recorded three dimensional representation of an actor in movement and to transmit to the stimulation element stimuli synchronized with the movement, the actor wearing a piece of clothing having the same material, color, shape, size and/or texture as the specific piece of clothing, the actor being located in front of a background having the same environment as the portable background, the recording being from the actor point of view,
 wherein the recorded three dimensional representation comprises a visual representation of the piece of clothing of the actor in movement, and
 wherein the controller synchronizes the transmission of stimuli from the stimulation element with movement of the specific piece of clothing.

2. The system of claim 1, whereby the three dimensional display comprises three dimensional glasses.

3. The system of claim 1, wherein the stimulation element comprises a vibrating element, the stimuli comprising a vibration.

4. The system of claim 1, wherein the stimulation element comprises an electrical element, the stimuli comprising an electrical signal.

5. The system of claim 1 further comprising a body support structure.

6. The system of claim 1 wherein the portable background comprises a tent.

7. The system of claim 1, wherein the specific piece of clothing comprises trousers a glove or a vest.

8. The system of claim 1, further including a mobile terminal, the mobile terminal comprising the controller.

9. The system of claim 1, wherein the movement comprises a movement of lower body limbs of the actor.

10. A method of neuro-rehabilitation, neuro-muscular training or rehabilitation comprising applying stimuli to a human to mimic an activity, the method comprising:
 selecting a body movement that involves a target muscle;
 displaying to the eyes of the human a three dimensional recording of the body movement from an actor point of view;
 transmitting stimuli to a body part of the human, the stimuli being synchronized with the body movement at the moment of the specific action; whereby
 the actor is wearing a piece of clothing having the same material, color, shape, size and/or texture as a specific piece of clothing worn by the human, and
 the human is facing a portable background having the same environment as the background facing the actor in the recording,
 wherein the recorded three dimensional representation comprises a visual representation of the piece of clothing of the actor in movement.

11. A method according to claim 10, the method further comprising a step of moving the body part of the human according to the selected body movement.

12. A method according to claim 10, further comprising a step of playing a voice recording describing the body movement to the human.

* * * * *